(12) United States Patent
Lee et al.

(10) Patent No.: US 8,389,225 B2
(45) Date of Patent: Mar. 5, 2013

(54) BIO-SILICA CHIP COMPRISING SILICA BINDING PROTEIN AND METHOD FOR FABRICATING THE SAME

(75) Inventors: Sang Yup Lee, Daejeon (KR); Tae Jung Park, Jeollanam-do (KR); Yang Kyu Choi, Daejeon (KR); Bon Sang Gu, Daejeon (KR); Jae Hyuk Ahn, Jeollanam-do (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 764 days.

(21) Appl. No.: 12/410,071

(22) Filed: Mar. 24, 2009

(65) Prior Publication Data

US 2010/0035362 A1 Feb. 11, 2010

(30) Foreign Application Priority Data

Mar. 24, 2008 (KR) ........................ 10-2008-0026803

(51) Int. Cl.
G01N 33/53 (2006.01)
G01N 31/00 (2006.01)

(52) U.S. Cl. ............ 435/7.21; 435/7.1; 436/1; 436/501; 436/518; 424/9.1; 424/520; 422/1; 422/430; 530/300; 530/350

(58) Field of Classification Search ........................ None
See application file for complete search history.

(56) References Cited

U.S. PATENT DOCUMENTS

2007/0112174 A1  5/2007  Shiba et al.

OTHER PUBLICATIONS

Shiryaev et. al. (Journal of Biological Chemistry, vol. 282, No. 29, Jul. 20, 2007, pp. 20847-20853).*
Brown (Nature Biotechnology, vol. 15, 1997, pp. 269-272).*
Weissbuch, I., et al., "Molecular Recognition at Crystal Interfaces", Science, 253(5020):637-645 (Aug. 9, 1991).
Miller, Jeffrey H., A short course in bacterial genetics: a laboratory manual and handbook for *Escherichia coli* and related bacteria, Plainview, NY: Cold Spring Harbor Laboratory Press, 1992.
Hentz, Nathaniel G., et al., "Bifunctional Fusion Proteins of Calmodulin and Protein A as Affinity Ligands in Protein Purification and in the Study of Protein-Protein Interactions", Analytical Chemistry, 68(22):3939-3944 (1996).
Brown, Stanley, "Metal-recognition by repeating polypeptides", Nature Biotechnology, 15:269-272 (1997).
Jordan, Claire E., et al., "Surface Plasmon Resonance Imaging Measurements of DNA Hybridization Adsoroption and Streptavidin/DNA Multilayer Formation at Chemically Modified Gold Surfaces", Analytical Chemistry, 69(24):4939-4947 (1997).
Brockman, Jennifer, et al., "A Multistep Chemical Modification Procedure to Create DNA Arrays on Gold Surfaces for the Study of Protein-DNA Interactions with Surface Plasmon Resonance Imaging", JACS, 121 (35):8044-8051 (1999).
Nelson, Bryce P., et al, "Surface Plasmon Resonance Imaging Measurements of DNA and RNA Hybridization Adsorption onto DNA Microarrays", 73(1):1 (2001).
Naik, Rajesh R., et al., "Silica-Precipitating Peptides Isolated from a Combinatorial Phage Display Peptide Library", Journal of Nanoscience and Nanotechnology, 2(1):95-100 (Feb. 2002) (abstract).
Braun, Rosemary, et al., "Genetically engineered gold-binding polypeptides: structure prediction and molecular dynamics", Journal of Biomaterial Science, 13:747-757 (2002).
Goodrich, Terry To, et al., "Direct Detection of Genomic DNA by Enzymatically Amplified SPR Imaging Measurements of RNA Microarrays", JACS, 126:4086-4087 (2004).
Hong, Soon Ho, et al., "The genome sequence of the capnophilic rumen bacterium *Mannheimia succiniciproducens*", Nature Biotechnology, 22:1275-1281 (2004).
Bradford, Marion M., "A Rapid and Sensitive Method for the Quantitation of Microgram Quantities of Protein Utilizing the Principle of Protein-Dye Binding", Analytical Biochemistry, 72:248-254 (1976).
Canziani, Gabriela, et al., "Exploring Biomolecular Recognition Using Optical Biosensors", Methods 19:253-269 (1999).
Hall, Damien, "Review—Use of Optical Biosensors for the Study of Mechanistically Concerted Surface Adsorption Processes", Analytical Biochemistry, 288:109-125 (2001).
Kukar, Thomas, et al., "Protein Microarrays to Detect Protein-Protein Interactions Using Red and Green Fluorescent Proteins", Analytical Biochemistry 306:50-54 (2002).

* cited by examiner

*Primary Examiner* — Lisa Cook
(74) *Attorney, Agent, or Firm* — Andrew D. Gerschutz; Tristan A. Fuierer; Moore & Van Allen, PLLC

(57) ABSTRACT

The present invention relates to a bio-silica chip comprising a silica-binding protein and a fabrication method thereof, and more particularly to a bio-silica chip in which a fusion protein of a silica-binding protein and a probe protein is immobilized on a chip comprising a silica layer, a fabrication method thereof and a method of using the bio-silica chip to detect interactions with biomaterials. The bio-silica chip will be very useful in biosensors, etc., because the bio-silica chip is advantageous in that it does not cause non-specific protein binding in the detection of protein-DNA, protein-ligand, protein-antibody, protein-peptide, protein-carbohydrate, protein-protein and cell-biomaterial interactions. Also, in the method for fabricating the bio-silica chip, a probe chip can be selectively immobilized on a silica device chip, which is widely used in biosensors, without a chemical surface treatment process. Thus, a chip fabricating process is simplified and a complicated process for purifying the probe protein becomes unnecessary, thus providing great improvements in productivity and economic efficiency.

5 Claims, 13 Drawing Sheets

FIG. 5
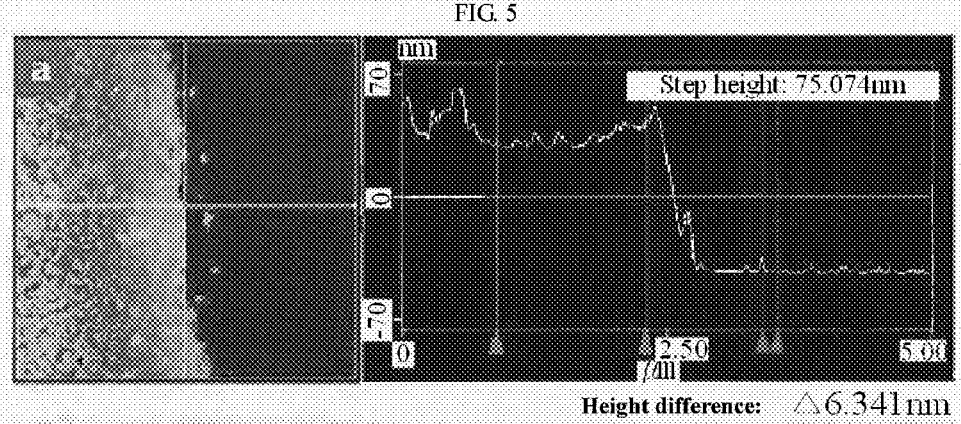
Height difference: △6.341nm
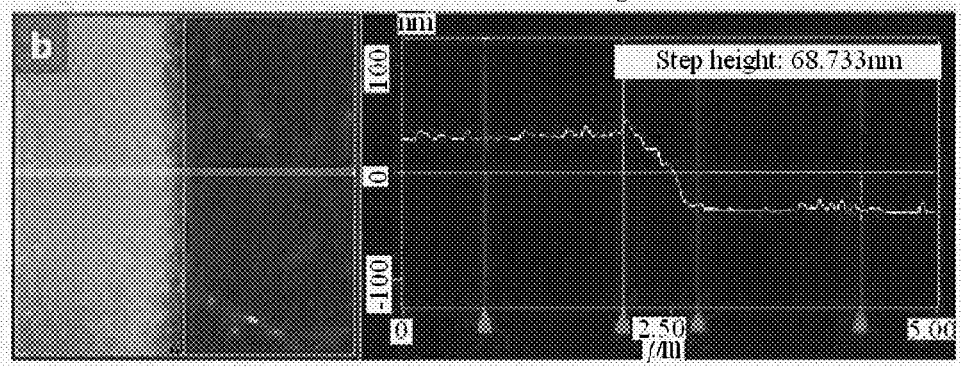

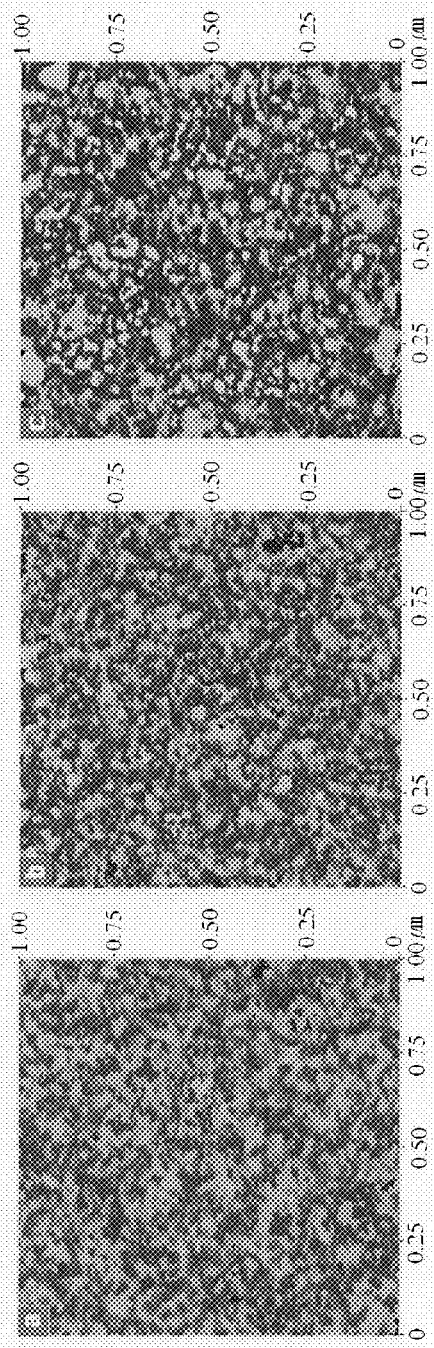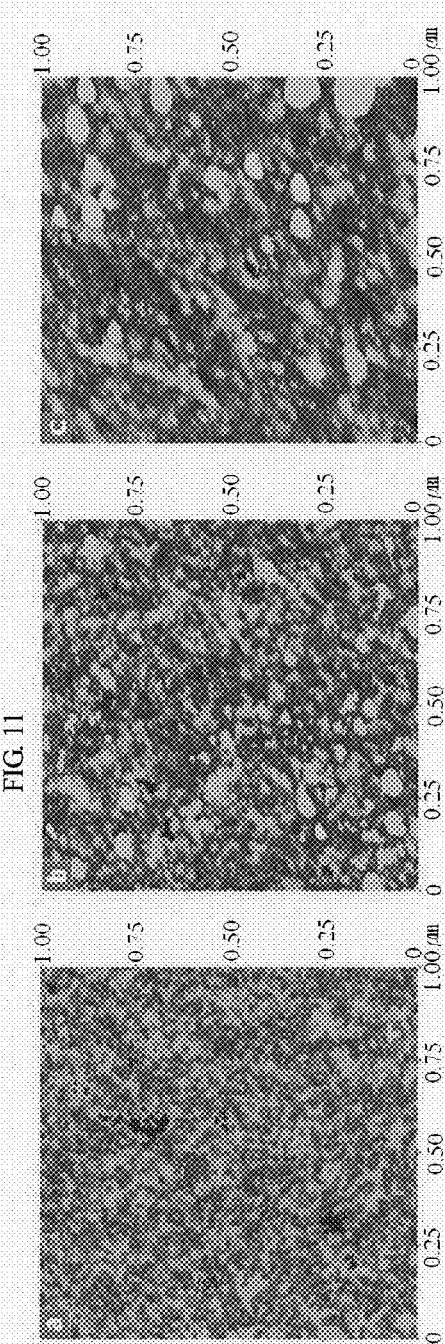

SEQUENCE LISTING

<160> NUMBER OF SEQ ID NOS: 24

<210> SEQ ID NO 1
<211> LENGTH: 12
<212> TYPE: PRT
<213> ORGANISM: Artificial
<220> FEATURE:
<223> OTHER INFORMATION: SBP3

<400> SEQUENCE: 1

Met Ser Pro His Pro His Pro Arg His His His Thr
1               5                   10

<210> SEQ ID NO 2
<211> LENGTH: 12
<212> TYPE: PRT
<213> ORGANISM: Artificial
<220> FEATURE:
<223> OTHER INFORMATION: SBP4

<400> SEQUENCE: 2

Arg Gly Arg Arg Arg Arg Leu Ser Cys Arg Leu Leu
1               5                   10

<210> SEQ ID NO 3
<211> LENGTH: 12
<212> TYPE: PRT
<213> ORGANISM: Artificial
<220> FEATURE:
<223> OTHER INFORMATION: SBP5

<400> SEQUENCE: 3

Lys Pro Ser His His His His Thr Gly Ala Asn
1               5                   10

<210> SEQ ID NO 4
<211> LENGTH: 60
<212> TYPE: PRT
<213> ORGANISM: Artificial Sequence
<220> FEATURE:
<223> OTHER INFORMATION: Mannheimia succiniciproducens MBEL55E rp1B2
      gene

<400> SEQUENCE: 4

Met Ala Ile Val Lys Cys Lys Pro Thr Ser Ala Gly Arg Arg His Val
1               5                   10                  15

Val Lys Ile Val Asn Pro Glu Leu His Lys Gly Lys Pro Tyr Ala Pro
            20                  25                  30

Leu Leu Asp Thr Lys Ser Lys Thr Gly Gly Arg Asn Asn Leu Gly Arg
        35                  40                  45

Ile Thr Thr Arg His Ile Gly Gly His Lys Gln
    50                  55                  60

<210> SEQ ID NO 5
<211> LENGTH: 72
<212> TYPE: PRT
<213> ORGANISM: Artificial Sequence
<220> FEATURE:
<223> OTHER INFORMATION: Mannheimia succiniciproducens MBEL55E rp1B2
      gene

<400> SEQUENCE: 5

Val Asp Val Leu Gly Lys Ala Gly Ala Asn Arg Trp Arg Gly Val Arg
1               5                   10                  15

```
Pro Thr Val Arg Gly Thr Ala Met Asn Pro Val Asp His Pro His Gly
         20                  25                  30

Gly Gly Glu Gly Arg Asn Phe Gly Lys His Pro Val Ser Pro Trp Gly
             35                  40                  45

Val Gln Thr Lys Gly Lys Lys Thr Arg His Asn Lys Arg Thr Asp Lys
 50                  55                  60

Tyr Ile Val Arg Arg Gly Lys
 65              70

<210> SEQ ID NO 6
<211> LENGTH: 132
<212> TYPE: PRT
<213> ORGANISM: Artificial Sequence
<220> FEATURE:
<223> OTHER INFORMATION: Mannheimia succiniciproducens MBEL55E rplB2
      gene

<400> SEQUENCE: 6

Met Ala Ile Val Lys Cys Lys Pro Thr Ser Ala Gly Arg Arg His Val
 1               5                  10                  15

Val Lys Ile Val Asn Pro Glu Leu His Lys Gly Lys Pro Tyr Ala Pro
             20                  25                  30

Leu Leu Asp Thr Lys Ser Lys Thr Gly Gly Arg Asn Asn Leu Gly Arg
         35                  40                  45

Ile Thr Thr Arg His Ile Gly Gly Gly His Lys Gln Val Asp Val Leu
 50                  55                  60

Gly Lys Ala Gly Ala Asn Arg Trp Arg Gly Val Arg Pro Thr Val Arg
 65                  70                  75                  80

Gly Thr Ala Met Asn Pro Val Asp His Pro His Gly Gly Glu Gly
                 85                  90                  95

Arg Asn Phe Gly Lys His Pro Val Ser Pro Trp Gly Val Gln Thr Lys
             100                 105                 110

Gly Lys Lys Thr Arg His Asn Lys Arg Thr Asp Lys Tyr Ile Val Arg
         115                 120                 125

Arg Arg Gly Lys
         130

<210> SEQ ID NO 7
<211> LENGTH: 36
<212> TYPE: DNA
<213> ORGANISM: Artificial
<220> FEATURE:
<223> OTHER INFORMATION: SBP3 gene

<400> SEQUENCE: 7
atgtctccgc atccacatcc acgtcatcac catacc                               36

<210> SEQ ID NO 8
<211> LENGTH: 36
<212> TYPE: DNA
<213> ORGANISM: Artificial
<220> FEATURE:
<223> OTHER INFORMATION: SBP4 gene

<400> SEQUENCE: 8
cgtggccgtc gtcgtcgtct gtcttgccgt ctgctg                               36

<210> SEQ ID NO 9
<211> LENGTH: 36
<212> TYPE: DNA
<213> ORGANISM: Artificial
<220> FEATURE:
```

<223> OTHER INFORMATION: SBP5 gene

<400> SEQUENCE: 9
aaaccgagcc accaccacca ccacaccggc gcgaac        36

<210> SEQ ID NO 10
<211> LENGTH: 180
<212> TYPE: DNA
<213> ORGANISM: Artificial Sequence
<220> FEATURE:
<223> OTHER INFORMATION: Mannheimia succiniciproducens MBEL55E rp1B1 gene

<400> SEQUENCE: 10
atggctatcg ttaaatgtaa gccgacctcc gctggtcgtc gtcacgttgt taaaatcgtg        60
aaccctgaat tacataaggg taaaccttac gcacctttat tagatactaa atctaaaact       120
ggtggtcgta ataatttagg acgtatcact actcgtcata tcggtggtgg tcataaacaa       180

<210> SEQ ID NO 11
<211> LENGTH: 216
<212> TYPE: DNA
<213> ORGANISM: Artificial Sequence
<220> FEATURE:
<223> OTHER INFORMATION: Mannheimia succiniciproducens MBEL55E rp1B2 gene

<400> SEQUENCE: 11
gtcgacgtac ttggtaaagc cggtgccaac cgctggagag gcgttcgccc tacagttcgc        60
ggtactgcga tgaacccggt agatcacccg cacggtggtg gtgaaggtcg taactttggt       120
aaacacccgg tatcaccttg gggcgttcaa accaaaggta agaaaactcg tcacaacaaa       180
cgtaccgata aatatatcgt acgtcgtcgt ggcaaa                                 216

<210> SEQ ID NO 12
<211> LENGTH: 396
<212> TYPE: DNA
<213> ORGANISM: Artificial Sequence
<220> FEATURE:
<223> OTHER INFORMATION: Mannheimia succiniciproducens MBEL55E rp1B2 gene

<400> SEQUENCE: 12
atggctatcg ttaaatgtaa gccgacctcc gctggtcgtc gtcacgttgt taaaatcgtg        60
aaccctgaat tacataaggg taaaccttac gcacctttat tagatactaa atctaaaact       120
ggtggtcgta ataatttagg acgtatcact actcgtcata tcggtggtgg tcataaacaa       180
gtcgacgtac ttggtaaagc cggtgccaac cgctggagag gcgttcgccc tacagttcgc       240
ggtactgcga tgaacccggt agatcacccg cacggtggtg gtgaaggtcg taactttggt       300
aaacacccgg tatcaccttg gggcgttcaa accaaaggta agaaaactcg tcacaacaaa       360
cgtaccgata aatatatcgt acgtcgtcgt ggcaaa                                 396

<210> SEQ ID NO 13
<211> LENGTH: 31
<212> TYPE: DNA
<213> ORGANISM: Artificial
<220> FEATURE:
<223> OTHER INFORMATION: primer 1

<400> SEQUENCE: 13
acaaaagctt ggcatcaccg gcacctggta c             31

-continued

<210> SEQ ID NO 14
<211> LENGTH: 28
<212> TYPE: DNA
<213> ORGANISM: Artificial
<220> FEATURE:
<223> OTHER INFORMATION: primer 2

<400> SEQUENCE: 14
ttaactcgag cggcttcacc ttggtgaa                              28

<210> SEQ ID NO 15
<211> LENGTH: 28
<212> TYPE: DNA
<213> ORGANISM: Artificial
<220> FEATURE:
<223> OTHER INFORMATION: primer 3

<400> SEQUENCE: 15
ggaattccat atggctatcg ttaaatgt                              28

<210> SEQ ID NO 16
<211> LENGTH: 29
<212> TYPE: DNA
<213> ORGANISM: Artificial
<220> FEATURE:
<223> OTHER INFORMATION: primer 4

<400> SEQUENCE: 16
atccaagctt ttgtttatga ccaccaccg                             29

<210> SEQ ID NO 17
<211> LENGTH: 34
<212> TYPE: DNA
<213> ORGANISM: Artificial
<220> FEATURE:
<223> OTHER INFORMATION: primer 5

<400> SEQUENCE: 17
ggaattccat atggtacttg gtaaagccgg tgcc                       34

<210> SEQ ID NO 18
<211> LENGTH: 31
<212> TYPE: DNA
<213> ORGANISM: Artificial
<220> FEATURE:
<223> OTHER INFORMATION: primer 6

<400> SEQUENCE: 18
acatgtcgac gtacttggta aagccggtgc c                          31

<210> SEQ ID NO 19
<211> LENGTH: 29
<212> TYPE: DNA
<213> ORGANISM: Artificial
<220> FEATURE:
<223> OTHER INFORMATION: primer 7

<400> SEQUENCE: 19
atccgtcgac ttgtttatga ccaccaccg                             29

<210> SEQ ID NO 20
<211> LENGTH: 31
<212> TYPE: DNA
<213> ORGANISM: Artificial
<220> FEATURE:
<223> OTHER INFORMATION: primer 8

<400> SEQUENCE: 20

```
acatgtcgac gtacttggta aagccggtgc c                                    31

<210> SEQ ID NO 21
<211> LENGTH: 68
<212> TYPE: DNA
<213> ORGANISM: Artificial
<220> FEATURE:
<223> OTHER INFORMATION: primer 9

<400> SEQUENCE: 21
aatactcgag gatcggacgg ttgctgcctt tccagttatc acgacaaagc tttttgccac     60
gacgacgt                                                              68

<210> SEQ ID NO 22
<211> LENGTH: 12
<212> TYPE: PRT
<213> ORGANISM: Artificial Sequence
<220> FEATURE:
<223> OTHER INFORMATION: Avian Influenza (H9N2 type) antigen

<400> SEQUENCE: 22

Cys Arg Asp Asn Trp Lys Gly Ser Asn Arg Pro Ile
1               5                   10

<210> SEQ ID NO 23
<211> LENGTH: 36
<212> TYPE: DNA
<213> ORGANISM: Artificial
<220> FEATURE:
<223> OTHER INFORMATION: Avian Influenza (H9N2 type) antigen gene

<400> SEQUENCE: 23
tgtcgtgata actggaaagg cagcaaccgt ccgatc                               36

<210> SEQ ID NO 24
<211> LENGTH: 24
<212> TYPE: PRT
<213> ORGANISM: Artificial
<220> FEATURE:
<223> OTHER INFORMATION: SBP3-AIa fusion peptide

<400> SEQUENCE: 24

Met Ser Pro His Pro His Pro Arg His His His Thr Cys Arg Asp Asn
1               5                   10                  15

Trp Lys Gly Ser Asn Arg Pro Ile
            20
```

BIO-SILICA CHIP COMPRISING SILICA BINDING PROTEIN AND METHOD FOR FABRICATING THE SAME

CROSS-REFERENCE TO RELATED APPLICATIONS

This application is filed under the provisions of 35 U.S.C. §119 (a) and claims the priority of Korean Patent Application No. 10-2008-0026803 filed on 24 Mar. 2008 entitled "Bio-Silica Chip Using Silica Binding Protein and Method for Fabricating the Same" in the name of Sang Yup LEE, et al., which is hereby incorporated by reference herein in its entirety.

BACKGROUND OF THE INVENTION

1. Field of the Invention

The present invention relates to a bio-silica chip comprising a silica-binding protein and a fabrication method thereof, and more particularly to a bio-silica chip in which a fusion protein of a silica-binding protein and a probe protein is immobilized on a chip comprising a silica layer, a fabrication method thereof, and a method for detecting interactions between biomaterials using the bio-silica chip.

2. Background of the Related Art

Recently, the functions of 10,000 genes among 100,000 predicted human genes were identified by the human genome project, and most of such genes are known to have direct connections to diseases. Also, because most diseases occur at the protein level rather than at the gene level, more than 95% of drugs, which have been developed to date or are being developed, target proteins. Thus, a protein sensor chip is a core technology in researches to find out the functions of biomolecules interacting specifically with a certain protein and to develop a method for treating and preventing diseases which was impossible to treat using classic methods, on the basis of the data obtained from protein function analysis and network analysis. Also, the protein sensor chip can selectively analyze small amounts of materials and can perform real-time measurement of the materials, and thus is widely used not only for the research of basic science, but also for the measurement of pollutants and the diagnosis of drugs or viruses.

A typical chip among biosensors including protein sensor chips is silica chips. In technologies on the analysis of protein-protein, DNA-RNA or carbohydrate-protein interactions using silica chips, which have been performed to date, a probe protein is immobilized on an affinity tag (Ni-NTA, Streptavidin, GST, etc.) or a silica chip surface after chemically modifying the silica chip surface with, for example, amine, ligand thiol or aldehyde, or by forming a self-assembly monolayer of a ligand having functional groups attached thereto. Alternatively, a probe protein is site-specifically immobilized using a technology of forming a uniform and stable monolayer of a biomolecule to control the orientation of the biomolecule at the molecular level. Using the immobilized probe protein, protein-protein interactions are analyzed using surface plasmon resonance (SPR) or the like (Hentz et al., *Anal. Chem.*, 68:3939, 1996; Kukar et al, *Anal. Biochem.*, 306:50, 2002; Hall D., *Anal Biochem.*, 288:109, 2001; Canziani, G. et al, *Methods*, 19:253, 1999; Brockman, J. M. et al, *JACS*, 121:8044, 1999; Nelson, B. P. et al, *Anal Chem.*, 73:1, 2001; Jordan, C. E. et al, *Anal Chem.*, 69:4939, 1997; Goodrich, T. T. et al, *JACS*, 126:4086, 2004).

However, although various biosensor technologies using silica chips as described above were developed, the technology for treating the surface of silica chips has great disadvantages in which a method for chemically treating the chip surface is complicated, and non-specific protein binding occurs. Also, it is difficult for this technology to be practically used, because proteins have weak binding ability and can be influenced by many chemical substances, thus causing many limitations in detecting protein-protein interactions. Furthermore, because high purity is required to immobilize the protein on the silica chip, a complicated purification process must be included, thus reducing economic efficiency Accordingly, there has been a need to develop a novel chip overcoming such shortcomings.

Moreover, the development of technology capable of selectively and stably immobilizing biomaterials on biosensor chips is required for the development of biosensors. Conventional methods for immobilizing biomaterials on biosensor chips are broadly classified into the following four methods: a method of physically or chemically adsorbing biomaterials onto the surface of the sensor chip, a method of covalently bonding biomaterials to the senor chip surface, a method of capturing biomaterials onto membranes, matrices, polymers, etc., and a method of immobilizing biomaterials on the sensor chip surface by inducing crosslinking between the biomaterials. Thus, there has been a need to develop a novel immobilization method different from such methods, which can selectively and stably immobilize biomaterials to the sensor chip surface.

Meanwhile, since it was known that, among silica-binding proteins (SBPs), a silica-binding protein consisting of 12 amino acids binds selectively to the surface of silica (Brown, S., *Nature Biotechnol.*, 15:269, 1997; Naik, R. R. et al., *J. Nanosci. Nanotechnol.*, 2:1, 2002), studies on SBP have been conducted. However, the exact mechanism by which on how SBP recognizes and binds to the silica surface is not yet found. It is predicted that the hydrophobic portion of the silica surface has a specific interaction with the hydrophobic region of the SBP sequence on the basis of molecular recognition (Braun, R., et al, *J. Biomater. Sci.*, 13:747, 2002).

Accordingly, the present inventors have made many efforts to provide a novel bio-silica chip overcoming the problems of the conventional silica chips, which can specifically and stably immobilize a probe protein, and is economical. As a result, the present inventors have isolated a novel silica-binding protein and found that a fusion protein of the isolated silica-binding protein and a probe protein is position-specifically immobilized on a silica chip, and the immobilized fusion protein can bind specifically to a target, thus making it possible to efficiently analyze the interaction, thereby completing the present invention.

SUMMARY OF THE INVENTION

It is an object of the present invention to provide a method capable of selectively and stably immobilizing a probe protein on a silica chip, and to provide a bio-silica chip which is economical and, at the same time, can efficiently analyze probe-target interactions.

Another object of the present invention is to provide a method for fabricating said bio-silica chip and a method for detecting a biomaterial using the bio-silica chip.

Still another object of the present invention is to provide a fusion protein of a novel silica-binding protein and a probe protein.

To achieve the above objects, the present invention provides a bio-silica chip in which a fusion protein of a silica-binding protein and a probe protein is immobilized on a chip comprising a silica layer.

The present invention also provides a silica-binding protein represented by an amino acid sequence of any one of SEQ ID NOS: 4 to 6, and a gene encoding the same.

The present invention also provides a fusion protein of a silica-binding protein and a probe protein, a recombinant vector containing a gene encoding the fusion protein, and a recombinant microorganism obtained by introducing the vector into a host cell selected from the group consisting of bacteria, fungi and yeasts.

The present invention also provides a method for fabricating a bio-silica chip, the method comprising: culturing said recombinant microorganism to express a fusion protein of a silica-binding protein and a probe protein; recovering the expressed fusion protein; and immobilizing the recovered fusion protein on a chip comprising a silica layer.

The present invention also provides a method for detecting an interaction with a target selected from the group consisting of DNAs, antibodies, peptides, proteins, and carbohydrates, which comprises using said bio-silica chip.

Other features and embodiments of the present invention will be more apparent from the following detailed description and the appended claims.

Figure 1:
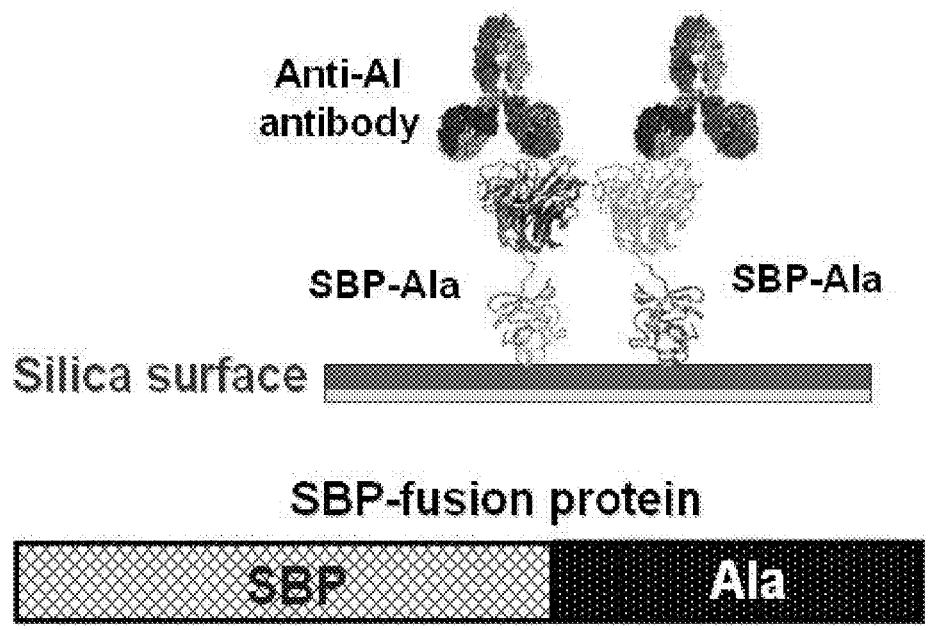
FIG. 1 is a schematic diagram of a bio-silica device chip and sensor system comprising the silica-binding protein (SBP) of the present invention and shows a detection system comprising a fusion protein of silica-binding protein (SBP) and avian influenza (AI) antigen (AIa).

FIG. 5 shows the results of atomic force microscopy (AFM) analysis showing the reaction of an rplB1-cSA fusion protein onto the surface of a silicon wafer (Si100). FIG. 5*a* is an AFM photograph of the silicon wafer surface, and 5*b* is a photograph taken after binding the fusion protein to the silicon wafer surface. A step height difference of about 6.3 nm is shown after binding.

FIG. 6 shows the results of atomic force microscopy (AFM) analysis showing the reaction of an rplB2-cSA fusion protein onto the surface of a silicon wafer (Si100). FIG. 6*a* is an AFM photograph of the silicon wafer surface, and FIG. 6*b* is a photograph taken after binding of the fusion protein to the silicon wafer surface. A step height difference of about 9.5 nm is shown after binding.

FIG. 7 shows measurement results for the response unit (RU) value of an SPR (Surface Plasmon Resonance) chip, which is obtained by allowing 25 μg/ml of an SBP3-AIa fusion protein (the fused form of silica-binding protein) to react on the SPR chip whose surface has been functionalized with silica.

FIG. 8 shows measurement results for the response unit (RU) value of an SPR (Surface Plasmon Resonance) chip, which is obtained by allowing various concentrations of rplB12-AIa fusion protein (the fused form of silica-binding protein) to react onto the SPR chip whose surface has been functionalized with silica. FIG. 8*a* is a graphic diagram showing the RU values obtained by allowing various concentrations of the rplB12-AIa fusion protein to react onto the SPR chip after functionalizing the surface of the SPR chip with (3-mercaptopropyl)trimethoxysilane, and FIG. 8*b* is an SPR sensorgrams for the results shown in FIG. 8*a*.

FIG. 9 is a graph showing the results obtained by allowing 25 μg/ml of an rplB12-AIa fusion protein to react with various concentrations of anti-AI antibody. FIG. 9*a* is a graph showing the RU values obtained by allowing the fusion protein to react with anti-AI antibody at various concentrations, and FIG. 9*b* is an SPR sensorgam obtained by allowing the fusion protein to react with anti-AI antibody of FIG. 9*a* at a concentration of 50 μg/ml in order to examine anti-AI antibody and anti-rabbit whole immunoglobulin G, respectively, following subsequently binding of the SBP-fusion protein.

FIG. 10 shows the results of the topographic surface morphologies by atomic force microscopy (AFM) analysis showing the reaction of a fusion protein with anti-AI antibody on the surface of a silicon wafer (Si100). FIG. 10*a* is a roughness analysis by AFM photograph of the silicon oxide surface, FIG. 10*b* is a photograph for the roughness analysis taken after binding the fusion protein to the silicon oxide surface, and FIG. 10*c* is a roughness analysis photograph by AFM taken after binding of 25 μg/ml SBP-AIa and 50 μg/ml anti-AI, sequentially.

FIG. 11 shows the results of the topographic surface morphologies by atomic force microscopy (AFM) analysis showing the reaction of a fusion protein with anti-AI antibody on the surface of silicon oxide ($SiO_2$). FIG. 11*a* is a roughness analysis by AFM photograph of the silicon oxide surface, FIG. 11*b* is a photograph for the roughness analysis taken after binding the fusion protein to the silicon oxide surface, and FIG. 11*c* is a roughness analysis photograph by AFM taken after binding of 25 μg/ml SBP-AIa and 50 μg/ml anti-AI, sequentially.

FIG. 12 is the three-dimensional structure of a field-effect transistor (FET) sensor designed in such a way that biomaterials are immobilized on the silica surface to detect electrochemical signals, which contains the silicon substrate (blue green), the source/drain (light green), the gate oxide (orange) and poly-crystalline silicon gate (light grey). SBP-AIa (violet) was immobilized in the vertical nanogap. The reaction of the SBP fusion protein with anti-AI antibody, which occurs on the surface of silicon oxide, can be measured by the change in electric current in a p-type silica substrate (silicon oxide).

FIG. 13 is a graphic diagram showing the results obtained by analyzing the change in electric current before and after immobilizing a SBP-AIa onto the surface of silicon oxide of a chip and sequential binding anti-AI antibody.

FIG. 14 is a graphic diagram showing the changes of voltage distribution obtained by measuring the change in electrochemical signals six times before and after immobilizing a SBP-AIa onto the surface of silicon oxide of a chip and sequential binding anti-AI antibody.

FIG. 15 is a graphic diagram showing selective binding of anti-AI antibody and anti-rabbit whole immunoglobulin G (IgG), respectively, following subsequently binding of the SBP-fusion protein.

DETAILED DESCRIPTION OF THE INVENTION, AND PREFERRED EMBODIMENT

Unless defined otherwise, all technical and scientific terms used herein have the same meaning as commonly understood by one of the ordinary skills in the art to which the invention pertains. Generally, the nomenclature used herein and the laboratory procedure described below are well known and commonly employed in the art.

The definition of important terms used in the detailed description of the invention and the like is as follows.

As used herein, the term "probe protein" refers to a protein or peptide which is immobilized on a protein chip and can bind to a specific material of interest in a sample added to the protein chip for analysis.

As used herein the term "target" refers to a specific material binding to the probe protein and is meant to include a polymer compound capable of binding to the immobilized probe protein, for example, peptide, protein or carbohydrate.

In one aspect, the present invention relates to a bio-silica chip comprising a fusion protein of a silica-binding protein and a probe protein.

In the present invention, the fusion protein is preferably immobilized on a chip comprising a silica layer, wherein the silica-binding protein of the fusion protein is specifically immobilized onto the silica surface. The chips comprising the silica layer are meant to include chips consisting only of silica layers and are preferably, but not limited to, FET devices, SPR devices or other electrochemical sensor devices. Also, the silica layer may be, but is not limited to, anyone selected from among a silicon oxide wafer, a polysilicon wafer, and a silicon wafer.

The silica-binding protein may bind either to the N-terminus or C-terminus of the probe protein or to the region between the N-terminus and C-terminus of the probe protein. The silica-binding protein may be used a monomeric form or a polymeric form, but is preferably used in a polymeric form, because polymers show a higher binding affinity.

In the present invention, as SBP3 (SEQ ID NO: 1), SBP4 (SEQ ID NO: 2) and SBP5 (SEQ ID NO: 3), sequences shown in the literature by Brown, S. were used. It is known that such SBPs consist of 12 amino acids and bind selectively to silica (Brown, S., *Nature Biotechnol*, 15:269, 1997).

```
SEQ ID NO 1:    H₂N-MSPHPHPRHHHT-COOH (SBP3)

SEQ ID NO 2:    H₂N-RGRRRRLSCRLL-COOH (SBP4)

SEQ ID NO 3:    H₂N-KPSHHHHHTGAN-COOH (SBP5)
```

In the present invention, novel silica-binding proteins represented by SEQ ID NOS: 4 to 6 were isolated from a *Mannheimia succiniciproducens* MBEL55E strain (KCTC0769BP, Hong et al., *Nature Biotechnol.*, 22:1275, 2004) and used after confirming the stable silica-binding ability thereof. However, it will be obvious to one skilled in the art that other known silica-binding proteins may be used in the present invention.

```
SEQ ID NO 4:
H₂N-MAIVKCKPTSAGRRHVVKIVNPELHKGKPYAPLLD

TKSKTGGRNNLGRITTRHIGGGHKQ-COOH (rplB1)

SEQ ID NO 5:
H₂N-VDVLGKAGANRWRGVRPTVRGTAMNPVDHPHGGGE

GRNFGKHPVSPWGVQTKGKKTRHNKRTDKYIVRRRGK-COOH (rplB2)

SEQ ID NO 6:
H₂N-MAIVKCKPTSAGRRHVVKIVNPELHKGKPYAPLLDT

KSKTGGRNNLGRITTRHIGGGHKQVDVLGKAGANRWRGVRPTVRGTAM

NPVDHPHGGGEGRNFGKHPVSPWGVQTKGKKTRHNKRTDKYIVRRRGK

-COOH (rplB12)
```

The silica-binding protein consisting of 60 amino acids (rplB1), 72 amino acids (rplB2) or 132 amino acids (rplB12; rplB1/rplB2 fusion) was shown to bind specifically to the surface of specific silicon oxide in the same manner as the SBPs. It is deemed that such silica-binding proteins may bind specifically to the surface of inorganic silica by chemical factors, such as hydrogen bonding, polarity or electronic effects, and structural characteristics such as size or shape (Weissbuch, I. et al, *Science,* 253:637, 1991), but the mechanism of selective binding to the silica surface was not exactly found. It is considered that the characteristics of cations such as arginine (Arg) and histidine (His) are involved in binding to the silica surface.

In the present invention, gene sequences represented by SEQ ID NOS: 7 to 8 were used as gene sequences encoding the silica-binding proteins represented by SEQ ID NOS: 1 to 3, respectively.

```
SEQ ID NO 7:
5'-ATGTCTCCGCATCCACATCCACGTCATCACCATACC-3'

SEQ ID NO 8:
5'-CGTGGCCGTCGTCGTCGTCTGTCTTGCCGTCTGCTG-3'

SEQ ID NO 9:
5'-AAACCGAGCCACCACCACCACCACACCGGCGCGAAC-

3'
```

In the present invention, gene sequences encoding novel silica-binding proteins represented by SEQ ID NOS: 4 to 6 are the following gene sequences represented by SEQ ID NOS: 10 to 12.

```
SEQ ID NO 10:
5'-ATGGCTATCGTTAAATGTAAGCCGACCTCCGCTGGTCG

TCGTCACGTTGTTAAAATCGTGAACCCTGAATTACATAAGGGTAAACCTT

ACGCACCTTTATTAGATACTAAATCTAAAACTGGTGGTCGTAATAATTTAG

GACGTATCACTACTCGTCATATCGGTGGTGGTCATAAACAA-3'

SEQ ID NO 11:
5'-GTCGACGTACTTGGTAAAGCCGGTGCCAACCGCTG

GAGAGGCGTTCGCCCTACAGTTCGCGGTACTGCGATGAACCCGGTAGAT

CACCCGCACGGTGGTGGTGAAGGTCGTAACTTTGGTAAACACCCGGTA

TCACCTTGGGGCGTTCAAACCAAAGGTAAGAAAACTCGTCACAACAA

ACGTACCGATAAATATATCGTACGTCGTCGTGGCAAA-3'

SEQ ID NO 12:
5'-ATGGCTATCGTTAAATGTAAGCCGACCTCCGCTGGT

CGTCGTCACGTTGTTAAAATCGTGAACCCTGAATTACATAAGGGTAAAC

CTTACGCACCTTTATTAGATACTAAATCTAAAACTGGTGGTCGTAATAAT

TTAGGACGTATCACTACTCGTCATATCGGTGGTGGTCATAAACAAGTCG

ACGTACTTGGTAAAGCCGGTGCCAACCGCTGGAGAGGCGTTCGCCCTA

CAGTTCGCGGTACTGCGATGAACCCGGTAGATCACCCGCACGGTGGTG

GTGAAGGTCGTAACTTTGGTAAACACCCGGTATCACCTTGGGGCGTTC

AAACCAAAGGTAAGAAAACTCGTCACAACAAACGTACCGATAAATATA

TCGTACGTCGTCGTGGCAAA-3'
```

In the present invention, the surface antigen of avian influenza was used as a probe protein, and a fusion protein of the probe protein and the silica-binding protein was expressed. Then, it was confirmed that, when a silica chip was treated with the fusion protein, the fusion protein was specifically immobilized on the silica chip, and when the silica chip was treated with an antibody to avian influenza antigen, the binding of the antibody to the silica chip also occurred. Particularly, when the silica chip was treated with the antibody together with other antibodies, binding to the other antibodies was hardly detected. This suggests that the bio-silica chip according to the present invention can specifically detect a target.

The present invention suggests that, when the silica-binding protein is used in the form of a fusion protein, it can be widely applied to biosensors in systems utilizing silica as a substrate. There has been no example in which the silica-binding protein is applied to a biosensor, and thus it is expected that, when the silica-binding protein is used, electrochemical, fluorescent and spectrophotometric detection using a biosensor will become easy.

In another aspect, the present invention relates to a method of fabricating a bio-silica chip using a silica-binding protein.

The method of the present invention comprises introducing into a host cell a recombinant vector containing a nucleic acid encoding a fusion protein of a silica-binding protein represented by an amino acid sequence of any one of SEQ ID NOS: 4 to 6 with a probe protein so as to obtain a recombinant microorganism, culturing the obtained recombinant microorganism to express the fusion protein of the silica-binding protein and the probe protein, recovering the expressed fusion protein, and immobilizing the recovered fusion protein on a chip comprising a silica layer. Herein, the host cell may be selected from the group consisting of bacteria, fungi and yeasts.

In the present invention, the immobilization of the fusion protein is preferably performed by a patterning method using microcontact printing, a microchannel method using a PDMS (polydimethylsiloxane) template, or a spotting method using microarrays.

In the present invention, the immobilization of the fusion protein may also be performed by collecting and disrupting the recombinant microorganism, purifying and recovering the fusion protein from the disrupted microorganism, and treating the chip comprising the silica layer, with the recovered fusion protein.

In the present invention, rplB12-AIa (a fusion protein of silica binding protein-probe protein) was expressed in a water-soluble form in *E. coli*, the *E. coli* strain was subjected to a simple cell disruption process to recover water-soluble fractions containing the fusion protein, and the silica device chip was treated with the collected fractions. In this case, it was shown that the fusion protein was specifically immobilized in a given direction, and it could be seen that, when the silica chip was treated with biomaterials such as antibodies, the interaction between the biomaterials was efficiently induced without reducing their binding ability.

In still another aspect, the present invention relates to a method for detecting an interaction with a target selected from the group consisting of DNA, antibodies, peptides, proteins, and carbohydrates, which comprises using the bio-silica chip.

In the present invention, the detection of the target is preferably performed by surface plasmon resonance (SPR) or SPR imaging. SPR is a technology allowing a reaction occurring on the chip surface to be sensitively analyzed by measuring changes in the refractive index using a glass chip coated with a thin silica film, without fluorescence labeling, and SPR imaging is a technology of imaging changes in the refractive index using CCD camera. The surface plasmon resonance (SPR) or SPR imaging is currently used as a common analysis method in biosensor systems and is used to detect protein-protein, protein-DNA or DNA-DNA interactions.

FIG. 1 is a schematic diagram of a bio-silica device chip and sensor system comprising the silica-binding protein (SBP) of the present invention, and shows a detection system comprising a fusion protein of silica-binding protein (SBP) and avian influenza (AI) antigen (AIa).

EXAMPLES

Hereinafter, the present invention will be described in further detail with reference to examples. It is to be understood, however, that these examples are for illustrative purposes only and are not to be construed to limit the scope of the present invention.

Particularly, although only the hydrophilic domain of neuraminidase (NA), which is avian influenza (AI) antigen (AIa), and streptavidin were illustrated as probe proteins in the following examples, it will be obvious to one skilled in the art that the same results can be obtained when other probe proteins are used.

Example 1

Isolation of Novel Silica-Binding Proteins

Among genes in a *Mannheimia succiniciproducens* MBEL55E strain (KCTC 0769BP), genes represented by SEQ ID NOS: 10 to 12, in which a base sequence consisting of bases 2003812-2004633 (NCBI GenBank accession no. NC 006300, Gene ID: 3075265) encoding rplB 50S ribosomal protein L2 encodes proteins having specific silica binding ability, were found. Particularly, a base sequence consisting of bases 2004454-2004633 was named "rplB1 gene" (SEQ ID NO: 10), a base sequence of bases 2003812-2004021 was named "rplB2 gene" (SEQ ID NO: 11), and a gene (rplB1-rplB2 fusion) was named "rplB12 gene" (SEQ ID NO: 12). Also, proteins derived from these genes were named "rplB1 (SEQ ID NO: 4) and rplB2 (SEQ ID NO: 5), respectively, and rplB12 (SEQ ID NO: 6; rplB1-rplB2 fusion) was used as a silica-binding protein. These proteins were fused with proteins which can be used as biosensors, thus applying as biosensors.

Example 2

Cloning of Gene Encoding Fusion Protein of Silica Binding Protein-Probe Protein 2-1: Cloning of SBP-cSA Gene In order to obtain a streptavidin gene using the genomic DNA of *Streptomyces avidinii* (KCTC9757) as template DNA, primers of SEQ ID NO: 13 and SEQ ID NO: 14 were used. For cloning, the cutting site of restriction enzyme HindIII was inserted into the primer of SEQ ID NO: 13, and the cutting site of restriction enzyme XhoI was inserted into the primer of SEQ ID NO: 14.

SEQ ID NO 13:
5'-ACAAAAGCTTGGCATCACCGGCACCTGGTAC-3' (primer 1)

SEQ ID NO 14:
5'-TTAACTCGAGCGGCTTCACCTTGGTGAA-3' (primer 2)

PCR was performed using the primers of SEQ ID NOS: 13 and 14, thus obtaining a streptavidin gene product. The PCR reaction was performed in the following conditions: pre-denaturation at 94° C. for 5 min, and then 30 cycles of denaturation at 94° C. for 1 min, annealing at 56° C. for 1 min and extension at 72° C. for 1 min, followed by final extension at 72° C. for 5 min.

The DNA obtained by PCR was electrophoresed on agarose gel to separate a 370-bp DNA fragment. The DNA fragment was digested with the restriction enzymes HindIII and XhoI, and then cloned into a plasmid pET-22b(+) (Novagen, Darmstadt, Germany) digested with the same restriction enzymes, thus constructing a recombinant plasmid pET-cSA.

PCR was performed using the genomic DNA of the *M. succiniciproducens* MBEL55E strain as a template and primers of SEQ ID NOS: 15 and 16, thus obtaining an rplB1 gene product. Also, an rplB2 gene product was obtained using primers of SEQ ID NOS: 17 and 18. Each of the gene products was digested with the restriction enzymes NdeI and HindIII, and then cloned into the above-constructed plasmid pET-cSA digested with the same restriction enzymes, thus constructing recombinant plasmids pET-rplB1-cSA and pET-rplB2-cSA-pET-cSA.

```
SEQ ID NO 15:
5'-GGAATTCCATATGGCTATCGTTAAATGT-3' (primer 3)

SEQ ID NO 16:
5'-ATCCAAGCTTTTGTTTATGACCACCACCG-3' (primer 4)

SEQ ID NO 17:
5'-GGAATTCCATATGGTACTTGGTAAAGCCGGTGCC-3'
(primer 5)

SEQ ID NO 18:
5'-ACATGTCGACGTACTTGGTAAAGCCGGTGCC-3' (primer 6)
```

Figure 2:
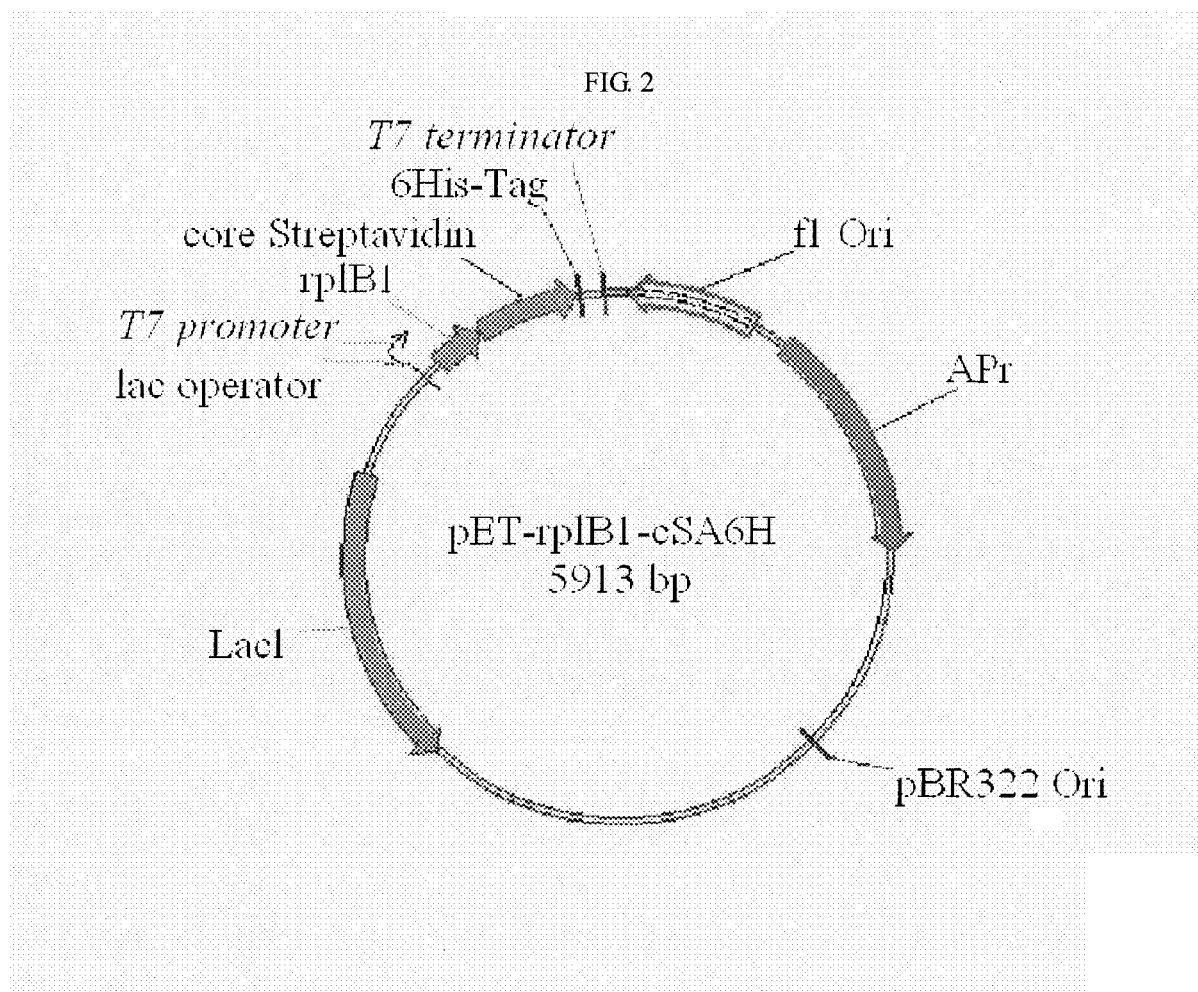
FIG. 2 is a gene map of plasmid pET-rplB1-cSA for expressing a fusion protein of silica-binding protein (SBP)-AIa fusion protein.
Figure 3:
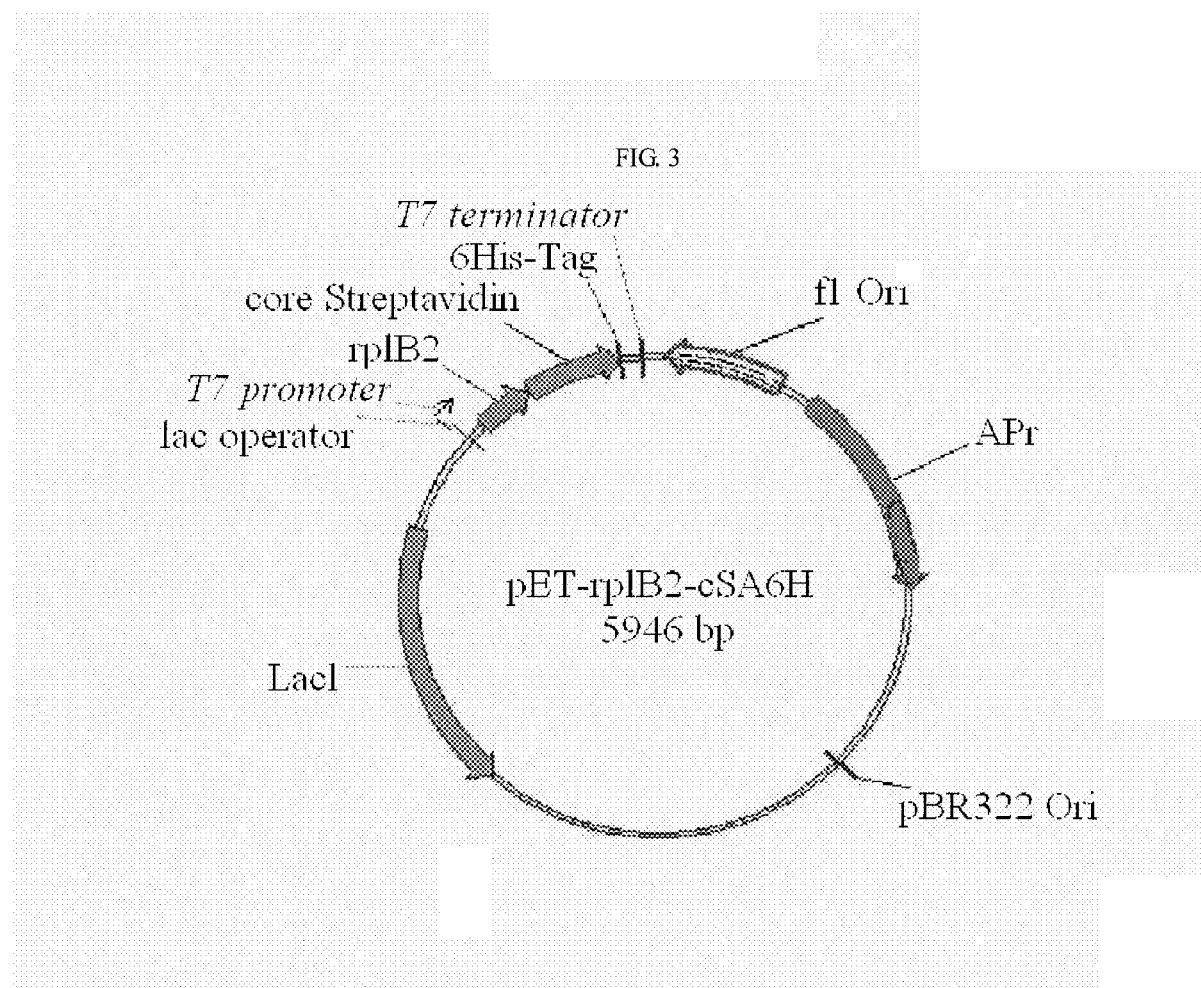
FIG. 3 is a gene map of plasmid pET-rplB2-cSA for expressing a fusion protein of silica-binding protein (SBP)-AIa fusion protein.
Figure 4:
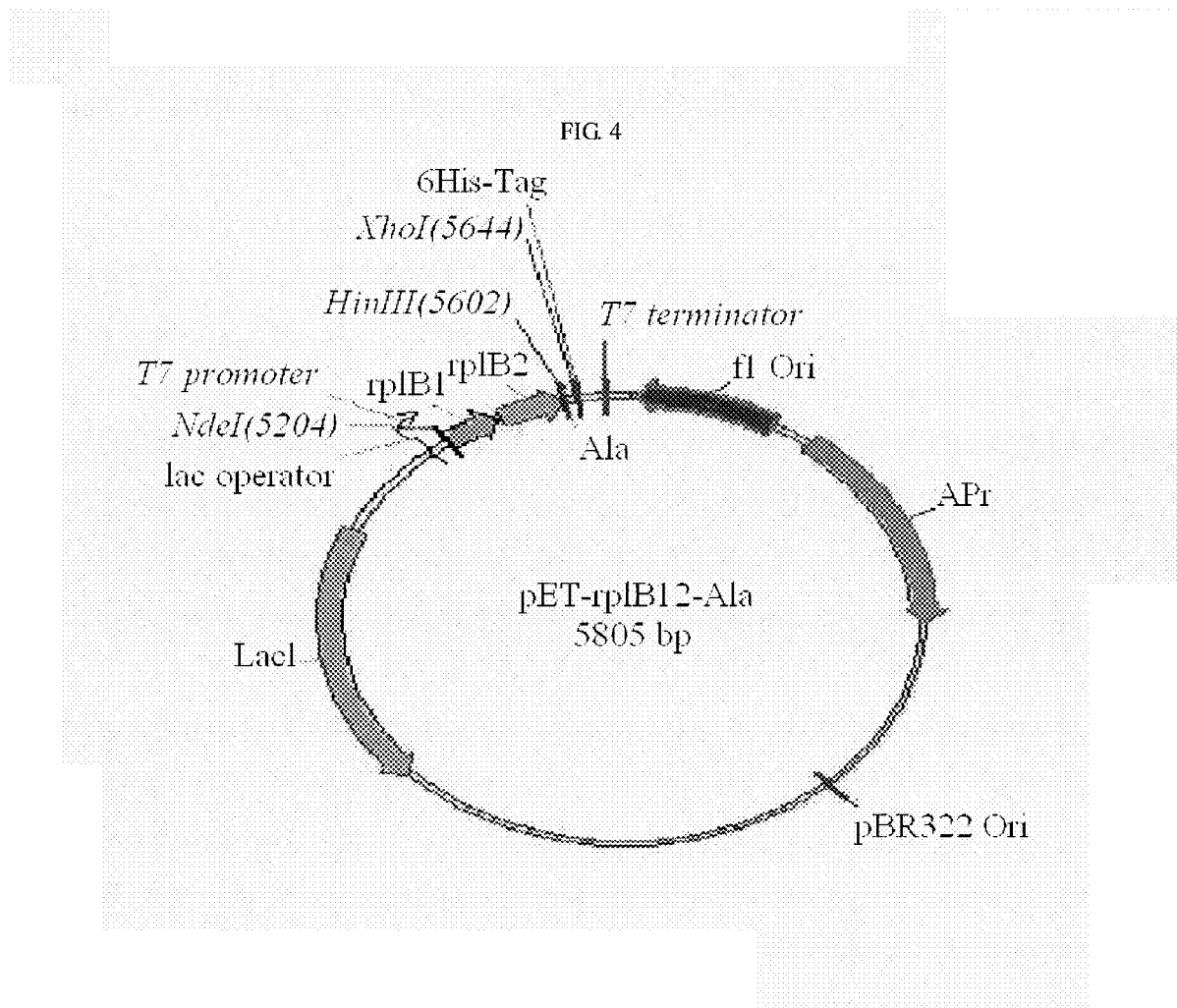
FIG. 4 is a gene map of plasmid pET-rplB12-AIa for expressing a fusion protein of silica-binding protein (SBP)-AIa fusion protein.

Each of the constructed recombinant plasmids pET-rplB1-cSA and pET-rplB2-cSApET-cSA was introduced into *E. coli* BL21(DE3) (Novagen, Darmstadt, Germany) using heat shock method, and the clones were screened in an LB medium plate (5 g/l of yeast extract, 10 g/l of trypton, and 10 g/l of NaCl) supplemented with 100 mg/l of ampicillin, thus preparing recombinant *E. coli* BL21 (DE3)/pET-rplB1-cSA and recombinant *E. coli* BL21 (DE3)/pET-rplB2-cSA. FIG. 2 shows a gene map of the constructed pET-rplB1-cSA, and FIG. 3 shows a gene map of the constructed plasmid pET-rplB2-cSA. In this Example, the SBP protein was bound to the N-terminus of streptavidin. However, it will be obvious to one skilled in the art that, even when the SBP protein is bound to the C-terminus of streptavidin according to the subject matter of the present invention, the same results can be obtained.

2-2: Cloning for Expression of SBP-AIa Fusion Protein

In order to clone a gene, which expresses a fusion protein of the novel silica-binding protein rplB12 (SEQ ID NO: 6) isolated in Example 1 and the hydrophilic domain of avian influenza antigen neuraminidase (NA) (hereinafter referred to as 'AIa'), into the recombinant *E. coli*, the genomic DNA of the *Mannheimia succiniciproducens* MBEL55E strain (KCTC 0769BP) was used as template DNA.

An rplB1 gene product was obtained by performing PCR using the genomic DNA of the *M. succiniciproducens* MBEL55E strain as a template and primers of SEQ ID NOS: 15 and 19, and an rplB2-AIa fusion gene product was obtained using primers of SEQ ID NOS: 20 and 21. The gene sequence of AIa could be obtained by selecting the gene sequence of H9N2 Korean avian influenza virus from among influenza viruses causing avian influenza, and constructing a novel base sequence (SEQ ID NO: 23) using the codon usage in *E. coli* (Miller, J. H., A short course in bacterial genetics. 1992) as a gene encoding 12 amino acids (amino acids 291-302; SEQ ID NO: 22) of NA. For cloning, the cutting site of restriction enzyme NdeI was inserted into the primer of SEQ ID NO: 15, and the cutting site of restriction enzyme SalI was inserted into the primer of SEQ ID NO: 19. Also, the cutting site of restriction enzyme SalI was inserted into the primer of SEQ ID NO: 20, and the cutting site of restriction enzyme XhoI was inserted into the primer of SEQ ID NO: 21.

```
SEQ ID NO 19:
5'-ATCCGTCGACTTGTTTATGACCACCACCG-3' (primer 7)

SEQ ID NO 20:
5'-ACATGTCGACGTACTTGGTAAAGCCGGTGCC-3' (primer 8)

SEQ ID NO 21:
5'-AATACTCGAGGATCGGACGGTTGCTGCCTTTCCAGT

TATCACGACAAAGCTTTTTGCCACGACGACGT-3' (primer 9)

SEQ ID NO 22:
H2N-CRDNWKGSNRPI-COOH (AIa)

SEQ ID NO 23:
5'-TGTCGTGATAACTGGAAAGGCAGCAACCGTCCGATC-

3'
```

The PCR reaction was performed in the following conditions: pre-denaturation at 94° C. for 5 min, and then 30 cycles of denaturation at 94° C. for 1 min, annealing at 56° C. for 1 min and extension at 72° C. for 1 min, followed by final extension at 72° C. for 5 min.

The DNA products obtained by PCR were electrophoresed on agarose gel to separate DNA fragments having sizes of about 180 bp (rplB1) and 280 bp (rplB2-AIa fusion). The separated fragments were digested with restriction enzymes NdeI and SalI for rplB1 and the restriction enzymes SalI and XhoI for rplB2-AIa. The DNA fragment was cloned into the plasmid pET-22b(+) (Novagen, Darmstadt, Germany) digested with the restriction enzymes NdeI and XhoI, thus constructing a recombinant plasmid pET-rplB12-AIa.

The constructed recombinant plasmid pET-rplB12-AIa was introduced into *E. coli* BL21(DE3) (Novagen, Darmstadt, Germany) using heat shock method, and the clones were screened in an LB medium plate (5 g/l yeast extract; 10 g/l tryptone, and 10 g/l NaCl) supplemented with 100 mg/L of ampicillin, thus preparing recombinant *E. coli* BL21(DE3)/pET-rplB12-AIa. FIG. 4 shows a gene map of the constructed plasmid pET-rplB12-AIa.

In this Example, the SBP protein rplB12 was bound to the N-terminus of AIa, but it will be obvious to one skilled in the art that, even when the SBP protein was bound to the C-terminus according to the subject matter of the present invention, the same results can be obtained.

Example 3

Expression of Fusion Protein of Silica Binding Protein-Probe Protein

*E. coli* BL21(DE3) constructed in Example 2-2, which was transformed with the recombinant plasmid pET-rplB12-AIa having a strong inducible T7 promoter, was cultured to express a rplB12-AIa fusion protein.

The T7 promoter induced gene expression by IPTG (isopropyl-β-thiogalactoside), and *E. coli* BL21(DE3) transformed with pET-rplB12-AIa was inoculated into a 500-ml flask containing 200 ml of LB liquid medium and cultured at 37° C. The gene expression of the pET-rplB12-AIa recombinant plasmid was induced by adding 1 mM of IPTG, when the optical density (OD) measured at a wavelength of 600 nm with a spectrophotometer reached 0.4.

At 4 hours after the induction of expression, the whole culture broth was centrifuged at 4° C. at 6,000 rpm for 5 minutes, the supernatant was discarded, and the remaining cells were washed once with 100 ml of TE buffer (10 mM Tris-HCl; 1 mM EDTA, pH 8.0), centrifuged again at 4° C. at 6000 rpm for 5 minutes, suspended in 100 ml of TE buffer (10 mM Tris-HCl; 1 mM EDTA, pH 8.0), and then disrupted with an ultrasonic cell disruptor at 4° C. The disrupted cell solution was centrifuged at 4° C. at 6,000 rpm for 30 minutes to remove insoluble proteins, and the remaining material was filtered through a 0.2-μm filter, thus obtaining a water-soluble protein fraction containing an rplB12-AIa fusion protein. The protein was quantified using the Bradford method (Bradford, M. et al., *Anal. Biochem.*, 72:248, 1976).

Example 4

Analysis of Silica Binding Affinity of Fusion Protein of Silica Binding Protein-Probe Protein The silica binding affinity of the rplB1 fusion protein and rplB2 fusion protein shown in Example 2-1 was analyzed using an atomic force microscope.

A silicon wafer (Si100, LG Siltron, Gumi, Korea) was treated with 50 μg/ml of each of the rplB1-cSA and rplB2-cSA fusion proteins and the fusion proteins were immobilized, and then observed with an atomic force microscope before treatment with the fusion protein (a) and after treatment with the fusion protein (b).

Figure 6:
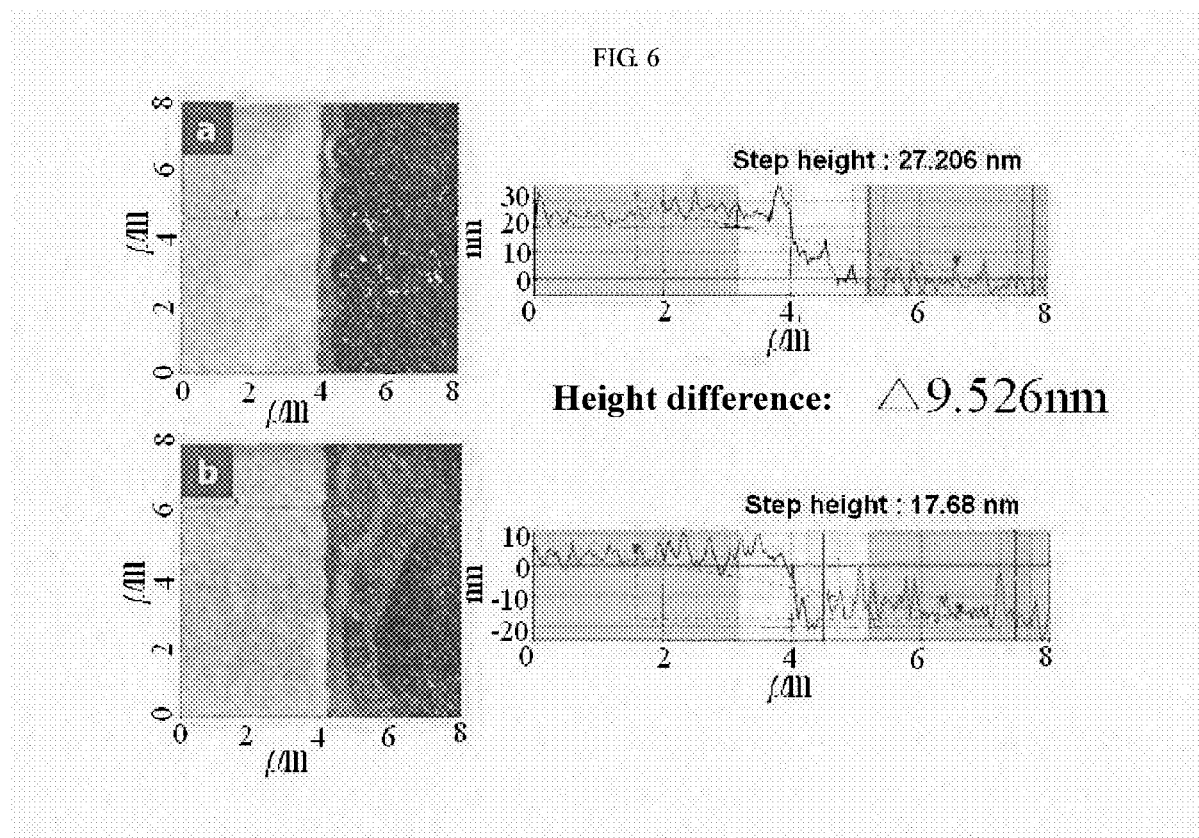

As it can be seen in FIG. 5 (rplB1-cSA fusion protein) and FIG. 6 (rplB2-cSA fusion protein), the surface morphology appearing by binding of biomaterials to the silicon wafer surface after reactions with the rplB1-cSA fusion protein and the rplB2-cSA fusion protein changed, and the step height of the surface changed while the fusion proteins were bound to the right side silicon surface to elevate the surface. In the case of the rplB1-cSA fusion protein, there was a step height difference of about 6.34 nm, suggesting that the rplB1-cSA fusion protein (about 20 kDa) was selectively bound to the silicon surface (FIG. 5). Also, in the case of the rplB2-cSA fusion protein, there was a step height difference of about 9.5 nm, suggesting that the rplB2-cSA fusion protein (about 22 kDa) was selectively bound to the silicon surface (FIG. 6).

Example 5

Fabrication of Bio-Silica SPR Chip Immobilized with Fusion Protein of Silica Binding Protein-Probe Protein and Detection of Target Using the Chip 5-1: Fabrication of Bio-Silica SPR Device Chip Immobilized with SBP3-AIa Fusion Protein Using silica binding protein SBP3, a bio-silica chip was fabricated. A peptide having a sequence of 24 amino acids (SEQ ID NO: 24), which is a fusion of the silica binding protein SBP3 (SEQ ID NO: 1) shown in the literature reported by Brown S. and an avian influenza antigen, was synthesized in Peptron Inc. (Daejeon, Korea), and the prepared peptide was dissolved in PBS buffer before use.

SEQ ID NO 24:    $H_2N$-MSPHPHPRHHHTCRDNWKGSNRPI-COOH (SBP3-AIa)

In order to immobilize the fusion protein on an SPR chip (Biacore AB, Uppsala, Sweden), the surface of the SPR chip was treated with silica by introducing 0.1 mg/ml of 3-mercaptopropyl)trimethoxysilane at a flow rate of 5 μl/min using a microchannel by a syringe pump in Biacore 3000 (Biacore AB) SPR analyzer. The SPR chip was sufficiently washed with washing buffer (phosphate-buffered saline, PBS, pH 7.4) at a flow rate of 5 μl/min, and then 25 μg/ml of the obtained SBP3-AIa fusion protein was introduced onto the SPR chip at a flow rate of 5 μl/min using a washing buffer (PBS, pH 7.4), thus immobilizing the fusion protein on the SPR chip surface functionalized with silica. Then, the chip was washed with washing buffer (PBS, pH 7.4), thereby fabricating a bio-silica SPR device chip.

Figure 7:
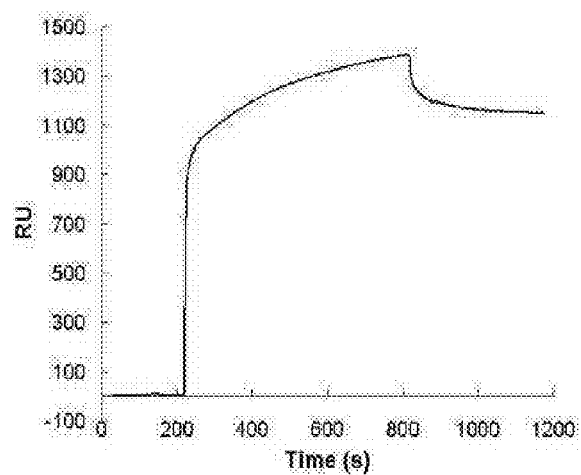

After SBP3-AIa which is a fused form of a silica binding protein was allowed to react on the SPR silica chip treated with (3-mercaptopropyl)trimethoxysilane, the response unit (RU) value of the SPR chip was measured. As a result, as shown in FIG. 7, the degree of binding of the fusion protein to the silica chip could be determined, and the silica chip showed a high RU value of more than about 1100 RU, suggesting that the fusion protein according to the present invention was effectively bound to the silica chip.

5-2: Fabrication of Bio-Silica SPR Device Chip Immobilized with rplB12-AIa Fusion Protein In order to immobilize the fusion protein on an SPR chip (Biacore AB, Uppsala, Sweden), the surface of the SPR chip was treated with silica by introducing 0.1 mg/ml of (3-mercaptopropyl)trimethoxysilane onto the surface at a flow rate of 5 μl/min using a microchannel by a syringe pump in a Biacore 3000 (Biacore AB) SPR analyzer. The SPR chip was sufficiently washed with washing buffer (phosphate-buffered saline, PBS, pH 7.4) at a flow rate of 5 μl/min, and then the purified rplB12-AIa fusion protein among the water-soluble protein fractions obtained in Example 3 was two-fold diluted in washing buffer (PBS, pH 7.4) from a concentration of 0.1 mg/ml. Then, each of the diluted samples was introduced onto the SPR chip at a flow rate of 5 μl/min, thus immobilizing the fusion protein on the SPR chip surface functionalized with silica. Then, the SPR chip was washed with washing buffer (PBS, pH 7.4), thereby fabricating a bio-silica SPR device chip.

Figure 8:
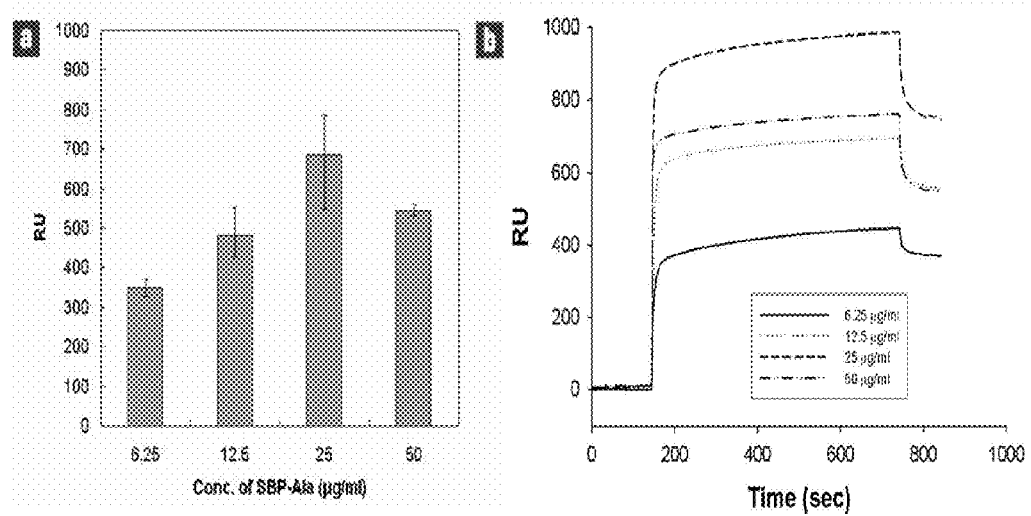

After the rplB12-AIa fusion protein which is a fused form of a silica binding protein was allowed to react at various concentrations on the SPR chip treated with (3-mercaptopropyl)trimethoxysilane, the response unit (RU) value of the SPR chip was measured. As a result, as shown in FIG. 8, the degree of binding of the fusion protein to the silica chip at various fusion protein concentrations could be determined, and the SPR chip showed generally high RU values, even though there was a difference between the fusion protein concentrations. This suggests that the fusion protein according to the present invention was effectively bound to the silica chip.

5-3: Detection of Antigen-Antibody Reaction Using Bio-Silica Chip

Anti-AI polyclonal antibody was allowed to react at various concentrations on the bio-silica chip fabricated in Example 5-2. The bio-silica SPR chip was immobilized with the rplB12-AIa fusion protein at a concentration of 25 μg/ml, and then washed with washing buffer (PBS, pH 7.4), and the anti-AI polyclonal antibody was analyzed after introducing each sample at various concentrations at a flow rate of 5 µl/min.

Figure 9:
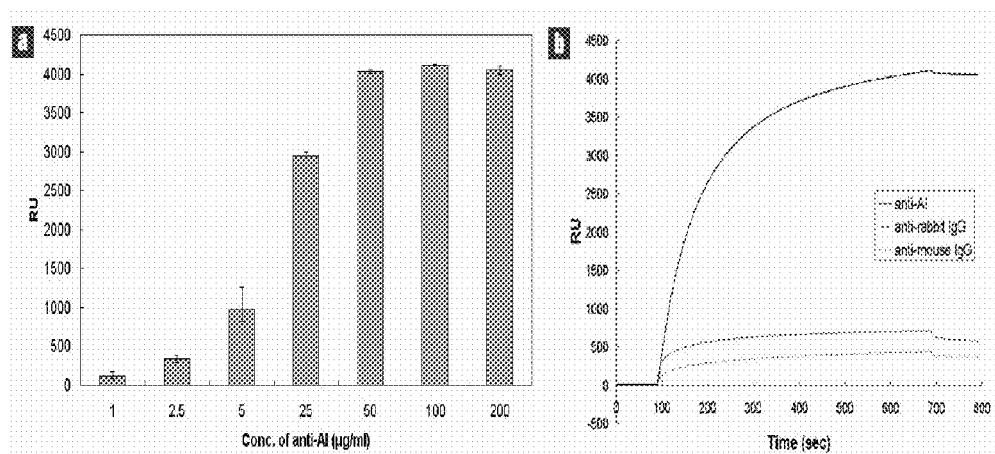

As a result, as shown in FIG. 9, when the response unit (RU) value of the SPR chip was measured, the reaction of the anti-AI polyclonal antibody was no longer increased at concentrations higher than 50 µg/ml (FIG. 9a). The SPR chip showed generally high RU values from a concentration of 1 µg/ml, suggesting that the fusion protein according to the present invention was effectively bound to the silica chip and would be used as a biosensor.

Also, 50 µg/ml of each of anti-AI polyclonal antibody, anti-rabbit IgG and anti-mouse IgG was allowed to flow onto the bio-silica SPR chip at a flow rate of 5 µl/min, and then analyzed.

As a result, as shown in FIG. 9b, when the anti-AI polyclonal antibody was used, it was detected, but when the anti-rabbit IgG and the anti-mouse IgG were used, they were hardly detected. Namely, it could be seen that the bio-silica chip according to the present invention could specifically detect the target.

5-4: Observation of Morphological Change by Antigen-Antibody Reaction on Silica Surface The reaction between biomaterials by an antigen-antibody reaction on the silica surface was analyzed using an atomic force microscope.

A silicon wafer (Si100, LG Siltron, Gumi, Korea) and silicon oxide (Aldrich, USA) was treated and immobilized with 50 µg/ml of rplB12-AIa fusion protein, and then treated with 50 µg/ml of anti-AI polyclonal antibody, and each reaction was carried out in a stirrer at 25° C. for 1 hour. Then, each of the silicon wafers and the silicon oxide was observed using an atomic force microscope before treatment with the fusion protein (a), after treatment with the fusion protein (b) and after treatment with the anti-AI polyclonal antibody (c).

As a result, as shown in FIG. 10 (silicon wafer) and FIG. 11 (silicon oxide), the morphology appearing by binding of biomaterials to the surface after sequential reactions with the rplB12-AIa fusion protein and the anti-AI polyclonal antibody became gradually larger. Namely, it could be seen that the rplB12-AIa fusion protein and the anti-AI polyclonal antibody were sequentially bound.

Example 6

Figure 12:
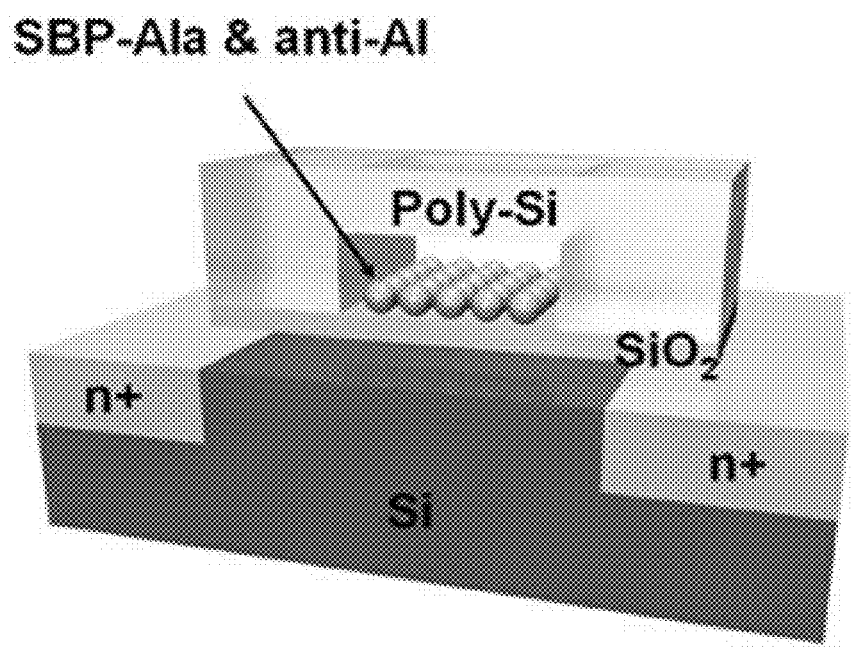

Fabrication of Bio-Silica FET Chip Immobilized with Fusion Protein of Silica Binding Protein and Probe Protein and Detection of Target Using the Chip 6-1: Fabrication of Bio-Silica FET Chip Immobilized with rplB12-AIa Fusion Protein and Measurement of Electrochemical Signal A FET (field-effect transistor) chip having a silica device as shown in FIG. 12 was fabricated. The device having a gap height of about 20 nm and a width of 2 µm was designed such that the fusion protein could be site-specifically immobilized on silicon oxide. The device can measure the change in electric current in a p-type silica substrate (silicon oxide). The device is characterized in that it detects a reaction by an electrical signal using voltage difference between before and after reaction with biomaterials.

The rplB12-AIa fusion protein obtained in Example 3 was diluted in PBS buffer to a concentration of 12.5 µg/ml and allowed to react on the FET chip having the silica device at room temperature for one hour. Then, the FET chip was washed three times with distilled water and dried in air, thus fabricating a bio-silica FET device chip. The bio-silica FET device chip thus fabricated can be used as a biosensor for detecting antibodies to avian influenza, and can be demonstrated by Example described below.

6-2: Detection of Antigen-Antibody Reaction in Bio-Silica Device Chip

All electrical signals in the chip fabricated in Example 6-1 were measured using a semiconductor parameter analyzer (HP4156C) immediately after inducing antigen-antibody reactions and then drying the device with nitrogen gas. The electrical signals were measured at a voltage of 0-4 V, and all the measurements were carried out on a probe station.

In order to examine whether the rplB12-AIa fusion protein and the anti-AI polyclonal antibody are selectively immobilized on the surface of silicon oxide in the device chip, the change in electrochemical signals was observed. In the experiment, 25 µg/ml of the rplB12-AIa fusion protein and 50 µg/ml of the anti-AI polyclonal antibody were suspended in PBS buffer before use, and in order to remove unbound samples after each reaction, PBS buffer was allowed to flow for 10 minutes, thus stabilizing the surface of the silica device chip.

Figure 13:
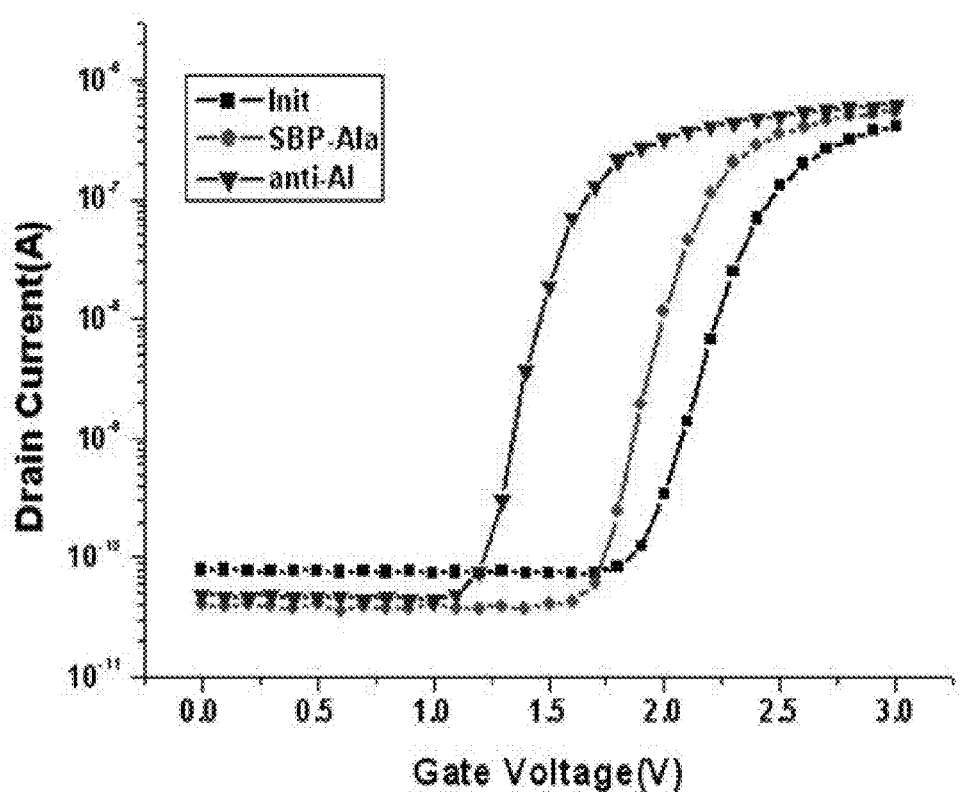
Figure 14:
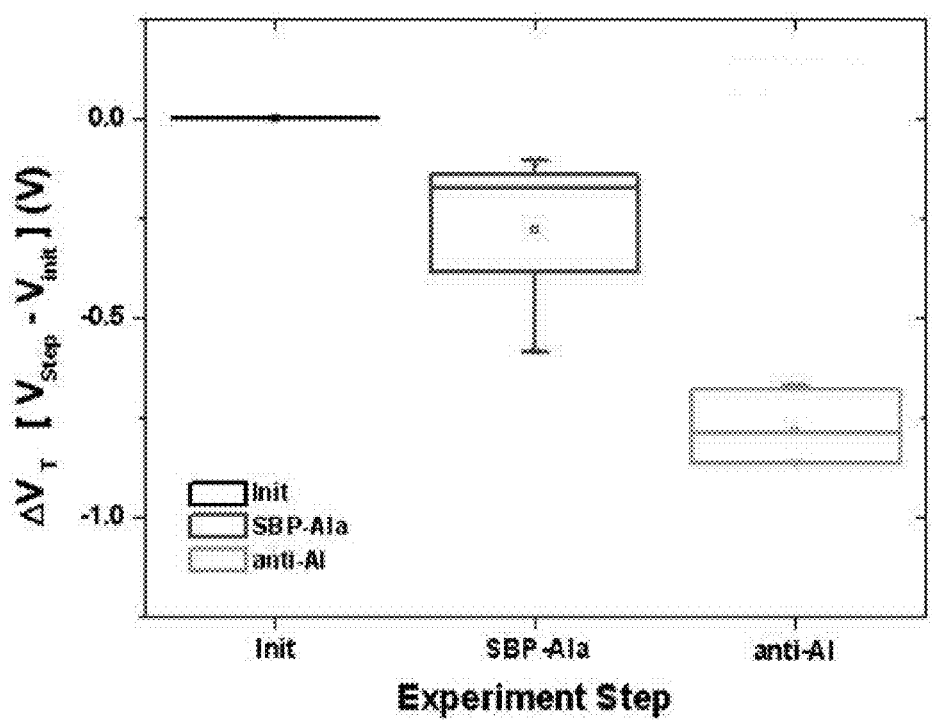

As a result, as shown in FIGS. 13 and 14, there were electrical signal changes of –0.23 V and –0.55 V after binding of the rplB12-AIa fusion protein (-●-, red line) and after binding of the anti-AI polyclonal antibody (-▼-, blue line), respectively, compared to a signal before reaction with the biomaterials (-■-, black line). Namely, it could be observed that the biomaterials were sensed by sequential reactions.

Also, in order to examine whether there is non-specific binding of antibody, the device chip was treated with anti-rabbit IgG as a control instead of the anti-AI polyclonal antibody in the same conditions.

Figure 15:
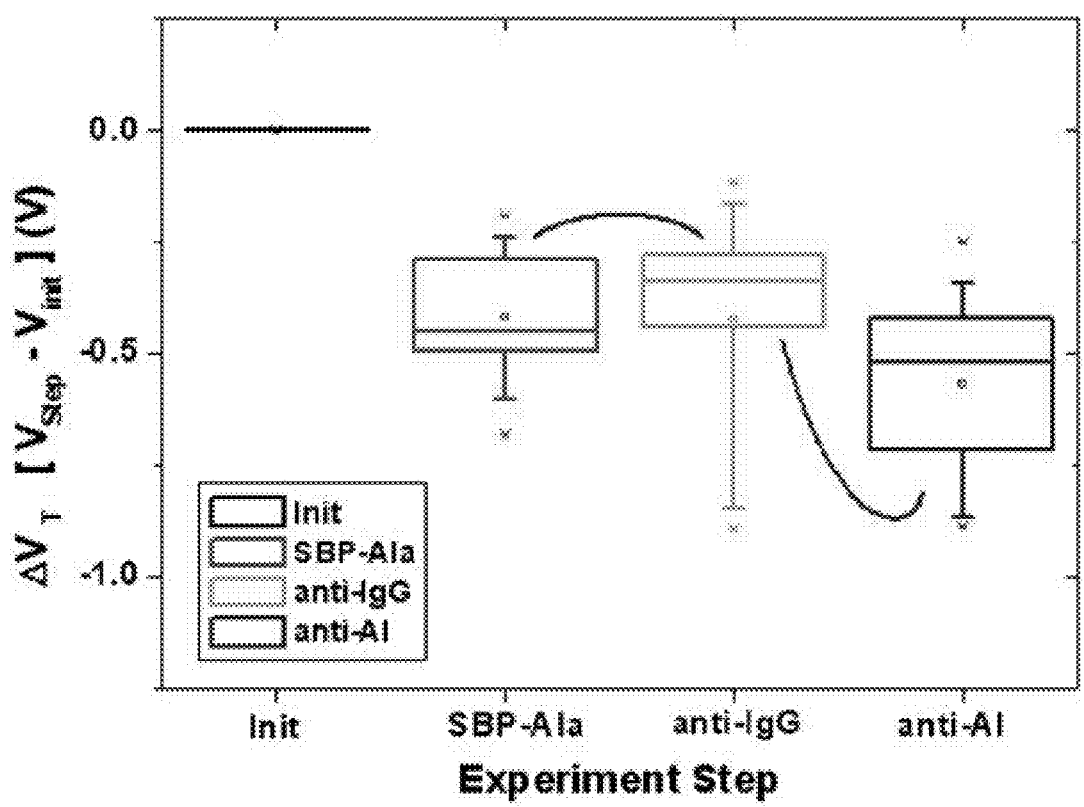

As a result, as shown in FIG. 15, an electrical signal for anti-rabbit IgG hardly changed compared to the electrical signal of the anti-AI polyclonal antibody. Accordingly, it could be confirmed that the silica device chip is a stable biosensor which does not cause non-specific binding on the surface thereof, and is a system capable of detecting antigen-antibody reactions.

INDUSTRIAL APPLICABILITY

As described in detail above, the bio-silica device chip according to the present invention is recyclable after a recovery process, and thus will also be suitable in biosensors for continuous analysis having high detection efficiency Also, the bio-silica chip is advantageous in that it does not cause non-specific protein binding in the detection of protein-DNA, protein-ligand, protein-antibody, protein-peptide, protein-carbohydrate, protein-protein and cell-biomaterial interactions. Due to such advantages, the bio-silica chip will be very useful in applying to biosensors, etc.

In addition, in the method for fabricating the bio-silica chip according to the present invention, a probe protein can be selectively immobilized on a silica device chip which is widely used in biosensors, without a chemical surface treatment process. Thus, a chip fabrication process is simplified and a complicated process for purifying the probe protein becomes unnecessary, thus providing great improvements in productivity and economic efficiency.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A bio-silica chip in which a fusion protein of a silica-binding protein and a probe protein is immobilized on a chip comprising a silica layer, wherein the silica-binding protein is a protein selected from the group consisting of SEQ ID NO: 4, SEQ ID NO: 5, and SEQ ID NO: 6.

2. The bio-silica chip according to claim 1, wherein the silica-binding protein binds either to the N-terminus or C-terminus of the probe protein or to the region between the N-terminus and C-terminus of the probe protein.

3. The bio-silica chip according to claim 1, wherein the probe protein is a surface antigen of avian influenza.

4. A method for fabricating a bio-silica chip, the method comprising:

culturing a recombinant microorganism to express a fusion protein of a silica-binding protein and a probe protein, wherein the silica-binding protein is a protein selected from the group consisting of SEQ ID NO: 4, SEQ ID NO: 5, and SEQ ID NO: 6;

recovering the expressed fusion protein; and immobilizing the recovered fusion protein on a chip comprising a silica layer.

5. The method for fabricating a bio-silica chip according to claim 4, wherein the immobilization of the fusion protein is performed by recovering and disrupting the recombinant microorganism, purifying and recovering the fusion protein from the disrupted microorganism, and treating the chip comprising the silica layer, with the recovered fusion protein.

* * * * *